United States Patent [19]
Giovanniello

[11] Patent Number: 5,356,609
[45] Date of Patent: Oct. 18, 1994

[54] METHOD FOR PREPARING BASIC ALUMINUM HALIDES BY REACTING ALUMINUM HALIDE WITH ALUMINUM

[75] Inventor: Rocco Giovanniello, Port Jervis, N.Y.

[73] Assignee: Westwood Chemical Corp., Middletown, N.Y.

[21] Appl. No.: 215,639

[22] Filed: Jul. 6, 1988

Related U.S. Application Data

[63] Continuation-in-part of Ser. No. 81,638, Aug. 3, 1987, Pat. No. 4,871,525, which is a continuation-in-part of Ser. No. 922,753, Oct. 24, 1986, abandoned, which is a continuation of Ser. No. 817,047, Jan. 8, 1986, abandoned.

[51] Int. Cl.$^5$ .................. A61K 7/38; C01F 7/56
[52] U.S. Cl. .................................. 423/462
[58] Field of Search .................. 423/462; 424/68

[56] References Cited

U.S. PATENT DOCUMENTS

| | | | |
|---|---|---|---|
| 2,196,016 | 4/1940 | Huehn et al. | 423/462 |
| 3,476,509 | 11/1969 | Jones | 423/462 |
| 3,507,896 | 4/1970 | Jones et al. | 423/462 |
| 3,891,745 | 6/1975 | Bellan et al. | 423/462 |
| 3,904,741 | 9/1975 | Jones et al. | 423/462 |
| 3,953,584 | 4/1976 | Danner et al. | 423/462 |
| 4,038,373 | 7/1977 | Merkl | 423/462 |
| 4,053,570 | 10/1977 | Merkl | 423/462 |
| 4,359,456 | 11/1982 | Gosling et al. | 423/462 |
| 4,859,446 | 8/1989 | Abratyn et al. | 423/467 |
| 4,871,525 | 10/1989 | Giovanniello et al. | 423/462 |
| 4,944,933 | 7/1990 | Inward | 423/462 |

FOREIGN PATENT DOCUMENTS

| | | | |
|---|---|---|---|
| 191628 | 8/1986 | European Pat. Off. | |
| 2048229 | 12/1980 | United Kingdom | 423/462 |

OTHER PUBLICATIONS

REACH® Reheis Enhanced Efficacy Aluminum Chlorohydrates.
Chemical Abstract vol. 51:15079b.

*Primary Examiner*—Jeffrey E. Russel
*Attorney, Agent, or Firm*—Anthony Lagani, Jr.

[57] ABSTRACT

Polymeric basic aluminum halides having the empirical formula:

$$Al_2(OH)_{6-y}X_y$$

where X is chlorine, bromine or iodine, y has a numerical value from 0.7 to 3, and whose polymer distribution as characterized by size exclusion chromatography is:
(a) 100% of the polymers are found in Bands II, III and IV, and
(b) Band III contains at least 25% of the polymer; are obtained by heating aluminum metal with $AlX_3 \cdot 6H_2O$ in water, where X is halogen.

36 Claims, 5 Drawing Sheets

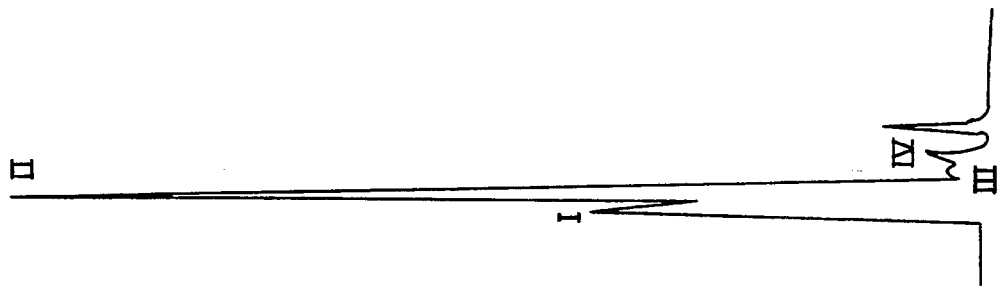

METHOD FOR PREPARING BASIC ALUMINUM HALIDES BY REACTING ALUMINUM HALIDE WITH ALUMINUM

CROSS-REFERENCE TO RELATED APPLICATIONS

This application is a continuation-in-part of U.S. patent application Ser. No. 081,638, filed Aug. 3, 1987, now U.S. Pat. No. 4,871,525, which is in turn a continuation-in-part of U.S. application Ser. No. 922,753, filed Oct. 24, 1986, now abandoned, which is itself in turn a continuation of U.S. patent application Ser. No. 817,047, filed Jan. 8, 1986, now abandoned.

FIELD OF THE INVENTION

This invention relates to basic aluminum halides. In particular, it relates to a process for preparing basic aluminum halide compositions having high antiperspirant activity and to the compositions prepared by the method of this invention. In particular this invention relates to a process for preparing basic aluminum halides by reacting an aluminum halide hexahydrate with aluminum metal.

BACKGROUND OF THE INVENTION

Basic aluminum halides (also referred to as aluminum halohydrates) have long been known to possess antiperspirant activity. These antiperspirant compositions are available in the form of polymeric compositions having the empirical formula:

$$Al_2(OH)_{6-y}X_y$$

wherein X is chlorine, bromine or iodine and y has a numerical value from about 0.7 to about 3. However, it is only in recent studies, as described in U.S. Pat. No. 4,359,456 (the '456 patent), that it has been shown by size exclusion chromatography that basic aluminum halides are composed of individual polymer bands which pertain to different molecular weight groups of the compound. In these studies of basic aluminum halides obtained by conventional methods of preparation it was shown that it can further be broken down from high molecular weight polymers into larger amounts of lower molecular weight polymers by diluting concentrated aqueous solutions thereof to lower aqueous concentrations and treating with heat and or aging at room temperature to produce more effective antiperspirants as shown in sweat reduction panel studies.

The U.S. Pat. No. '456 patent describes processes for the preparation of improved antiperspirant compositions of aluminum halohydrates, which involve heating a 2.5 to 8.5% by weight, based on aluminum, of an aqueous solution of an aluminum halohydrate of the formula:

$$Al_2(OH)_{6-y}X_y$$

where X and y are as defined above, at a temperature of 50° to 140° C. for a period of time to impart to the aluminum product certain desired properties in respect of size exclusion chromatogram test bands. The products thus obtained from these processes have good antiperspirant activity, but the processes do not provide compositions containing larger amounts of the lower molecular weight polymers with a narrow polydispersity which are believed to possess greater antiperspirant activity.

In addition to the U.S. Pat. No. '456 patent, processes for the preparation of antiperspirant basic aluminum halides are shown in U.S. Pat. Nos. 3,507,896; 3,891,745; 3,904,741; 4,038,373 and 4,053,570. However, none of these patents disclose polymeric compositions possessing the desired amounts of the lower molecular weight polymers as measured by the size exclusion chromatogram test band.

SUMMARY OF THE INVENTION

It has surprisingly been found that polymeric basic aluminum halides having the empirical formula:

$$Al_2(OH)_{6-y}X_y \cdot nH_2O$$

wherein y has a numerical value from about 0.7 to about 3, X is chlorine, bromine or iodine; n is a numeral from about 0.8 to about 4.0 and the polymer distribution as characterized by size exclusion chromatogram test is: (a) 100% of the aluminum containing polymers are found in bands II, III and IV, and (b) band III contains at least 25% of the polymers, can be prepared by reacting an aluminum metal with an aluminum halide compound having the formula $AlX_3 \cdot 6H_2O$ where X is as previously defined, while maintaining the temperature of the reaction mixture at about 50° C. to about 100° C. The aluminum metal is preferably in the form of pellets or powder.

The amount of water used is such as to have the final concentration of the polymer solution, in percent by weight, in the range of about 8 to about 25%, preferably about 15 to about 25%, and more preferably from about 17 to about 22% by weight. The reaction temperatures are preferably in the range of about 95° to about 100° C.

BRIEF DESCRIPTION OF THE DRAWINGS

FIG. 1 is a chromatogram of a product made by a known conventional method as described in Example 1.

DETAILED DESCRIPTION OF THE INVENTION

Figure 2A:
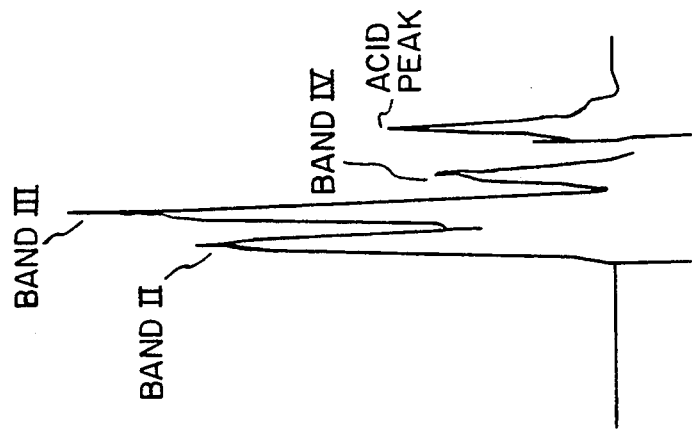
FIG. 2A-F is a chromatogram of 20% aqueous aluminum chlorhydrate prepared according to the process of this invention by reacting aluminum chloride hexahydrate, water and aluminum at 95° C. for seven days in accordance with Example 2.

This invention relates to an improved method for preparing an aluminum chlorhydrate having improved antiperspirant activity as determined by the existence of a band III component of polymer of at least 25 wt. %. The product of this invention is substantially free of any Band I component.

While the product of this invention can be defined as having the empirical formula $Al_2(OH)_{6-y}X_y$, where y is 0.7 to 3 and X is Cl, Br or I, it will be understood that the aluminum halohydrate of this invention has associated with it both free water and coordinated water. The empirical formula showing this water is $Al_2(OH)_{6-y}X_y \cdot nH_2O$, where y and X are as previously defined and n has a numerical value of about 0.8 to about 4; preferably about 1 to about 3.5; more preferably about 2 to about 3. In its preferred embodiment y is about 1 to 2. The products of this invention are distinguished from prior art basic aluminum halides in that 100% of the aluminum containing polymers are found in Bands II, III and IV, with substantially no part of the product found in Band I. A preferred product of this invention has the empirical formula $Al_2(OH)_5X \cdot nH_2O$ wherein X and n are as previously defined. Approximately 85 wt. % of the water is coordinated water as contrasted with conventional Aluminum Chlorhydrate which contain about 60% coordinated water.

The process comprises reacting metallic aluminum in the form of pellets, powder, chips or bars with a aluminum halide having the formula $AlX_3 \cdot 6H_2O$, where X is chlorine, bromine or iodine. Preferably the halide is aluminum chloride.

While the reaction can be carried out at a temperature of about 50° C. to about 100° C., it is preferred that the reaction is carried out at about 80° C. to about 100° C.; more preferably at about 90° C. to about 100° C.; most preferably at about 95° C. to about 100° C., e.g., about 96° C. to about 98° C. The reaction is carried out in the absence of reflux conditions. Refluxing can result in reduced formation of the Band III component, and will result in the formation of pre-Band I high molecular weight polymers. However, it is within the scope of this invention to utilize a condenser to condense and return water evaporated during the process to the reaction vessel in order to maintain the proper concentration of reactants and product in the reaction mixture.

Generally, an excess of aluminum is used in carrying out the reaction process of this invention. This is so since aluminum must always be present throughout the reaction in order for the final product to be formed. However, where the aluminum is in a powdered form the reaction will go to completion using stoichiometric amounts of aluminum and aluminum halide hexahydrate based on the anticipated formula of the product. For example, where the desired product is $Al_2(OH)_5Cl$ the $AlCl_3 \cdot 6H_2O/Al$ ratio is determined based on that formula for aluminum chlorohydrate, and not on the stoichiometric amounts required to form aluminum chloride.

In carrying out the process of this invention the aluminum is preferably in pellet or powder form. While chemically pure aluminum can be utilized in the practice of this invention it is not preferred. The aluminum of choice contains trace amounts of iron or copper. The iron and copper catalyze the $AlX_3 \cdot 6H_2O$-Aluminum reaction, which results in substantial heat generation, thereby minimizing the amount of heating required to maintain the reaction mixture at the proper temperature.

Although the concentration of iron in the aluminum can range from about 0.02 to about 0.25 wt. % in the preparation of concentrated solutions of aluminum chlorhydrate of the prior art, in the practice of this invention the iron concentration in the aluminum must be limited to about 0.02 to about 0.1 wt. %. Reactions which use aluminum having iron impurities of greater than 0.1% result in aluminum salts having iron contents greater than the acceptable limits of the cosmetics trade. The concentration of copper in the aluminum can be about 0.005 to about 0.2 wt. %. Preferably, however, the copper content of the aluminum is about 0.005 to about 0.03 wt. %. It is of course within the scope of this invention to utilize aluminum metal containing both iron and copper.

A critical aspect of the process of this invention is the final concentration of aluminum halohydrate in the reaction mixture which must be maintained at a concentration in percent by weight in the range of about 8 to about 25%, preferably about 15 to about 25%, and more preferably from about 17 to about 22% by weight. Above 25 wt. % the amount of Band III in the product diminishes. For example at a 35% concentration the Band III component is reduced to about 20% for an aluminum chlorhydrate. While the Band III levels will be higher where the halogen is bromine, Aluminum Bromhydrate is not the most preferred product.

The process can be successfully practiced over the entire 8 to 25 wt. % range. It is preferred, however, that the minimum concentration be at least 15 wt. %. Below 15% the solutions of product are cloudy. There appears to be a relationship between the cloudiness of the reaction solution and the development of higher molecular weight species found prior to Band II in the chromatographic distribution. When reactions are carried out in solutions having a concentration of less than 15%, the development of cloudiness can be avoided by reducing the reaction temperature and shortening the reaction time. Preferably the reaction time is about 1 hour to about 100 hours. Where the solution concentration is below 15% it is preferred that the reaction temperature is below 90° C. and that the reaction time is less than 24 hours; more preferably the reaction temperature is about 70° to about 85° C., e.g., 80° C.

The polymer distribution achieved by the process of this invention is one of extremely narrow polydispersity, particularly when the final batch concentration of aluminum halohydrate falls within the range of 17–22% and the metal to halogen atomic ratios are about 1.00:1 to about 2.10:1. Preferably these ratios are about 1.50:1 to about 2.00:1; more preferably about 1.90:1 to about 2.00:1. Such products derived from the process of this invention can be converted to more stable polymer forms by the hot spray drying of the solution of aluminum chlorohydrate to a dry powder utilizing conventional spray drying methods.

Spray drying is the preferred method of converting the hot aqueous basic aluminum salts of this invention to a stable powdered form. Other methods of drying such as tray drying or vacuum drying require longer periods of time for water evaporation. These drying techniques go through concentrated liquid phases, or reduced temperatures, both of which can result in a substantial loss in the Band III component of the product of this invention.

In carrying out the spray drying process the outlet drying temperature can be about 150° F. to about 275° F.; preferably about 200° F. to about 240° F.; more preferably about 210° F. to about 230° F. If the aluminum halohydrate solution is allowed to cool after completion of the reaction, and before spray drying a loss in the Band III component to a level of less than 20% results. It is preferred that the solution be filtered before spray drying.

The size exclusion chromatogram test was used to determine polymer distributions, contents and relative retention times of Bands I, II, III and IV on the samples of the compositions of this invention and samples of known compositions. This test is an analytic technique related to high performance liquid chromatography (HPLC). In carrying out the tests a Waters Associates Model 510 pump, a U6K injector, a 401 refractive index detector, and a 730 data module were used for the HPLC instrumentation. Two micro Porasll 60 Å GPC columns 3.8×30 cm (Waters Cat. No. 84190) were used in the adsorption.

The directions for carrying out the test are as follows:

In preparing the mobile phase, pipette 2 ml. conc. nitric acid in a 1 l. volumetric flask containing distilled water, dilute to mark and mix. New columns should be conditioned with this mobile phase at least three hours prior to sample testing. Turn pump on to 1.0 ml/min., flush the reference side of the refractive index cell several minutes and switch to sample side. Referring to the operator manual, zero in the R.I. detector and set the attenuation to 16X. Also set the 730 data module to the following parameter values:

| Parameter No. | Description | Value |
| --- | --- | --- |
| 2 | Chart Speed | 0.6 (cm./min.) |
| 3 | Plot Mode | 0 (Off) |
| 4 | Pen 2 | 0 (Off) |
| 5 | Pen 1 | 10 |
| 7 | Auto Zero | 0 (Off) |
| 8 | L.C. Mode | 1 (Yes) |
| 9 | Calibration | 0 (Analysis) |
| 20 | Auto Parameters | 0 (Off) |
| 21 | Peak Width | 7 |
| 22 | Noise Rejection | 2,000 |
| 23 | Area Rejection | 1,000 |
| 24 | Run/Stop | 6.5 (Min.) |
| 33 | Report % results | 1 (Yes) |
| 46 | Flow Rate | 1.0 (ml./min.) |
| 47 | Pressure | Column Pressure |
| 48 | Detector/Attenuation | 401/016 |
| 63 | Report Percent Only | 1001 |

The analytical procedure is as follows:

Pipette 0.2 ml. 12M hydrochloric acid into a 25 ml volumetric flask containing distilled water, dllute to mark and mix.

After the detector and columns have reached equilibrium as seen by the stability of the response on parameter 51, set parameter 51 to read 5,000–10,000 by turning the optical zero knob on the detector, being certain that operating temperatures within the room remain constant since the slightest change in the temperatures will be sensed by the R.I. detector which will create a baseline drift.

Inject a 15 $\mu l$. sample of 0.1N hydrochloric acid standard and observe its retention time (the retention time in this analytical test was found to be 5.70 minutes). Set parameters 81 and 82 to retention time values off 5.40 and 6.00 minutes which will inhibit and resume integration without integrating the hydrochloric acid band itself which contains no aluminum polymers.

Dilute all basic aluminum halides to approximately a 10% active level with distilled water, filter the sample through a 0.45 m filter and inject a 3.0 $\mu l$ sample for the test. The chromatogram will show which aluminum containing polymer bands are present, the retention times of each band and their calculated percentages.

Calculation:

% Band to be determined =

$$\frac{\text{(Area Percent of band to be determined)}}{\text{Total Area Percent of } Al \text{ containing bands}}$$

It is known that during stages of basic aluminum halides synthesis via conventional methods of preparation, higher molecular weight polymers, pertaining to aluminum polymers of the Band I range, are developed and their percent composition against the total polymer content increases with increasing metal to chloride atomic ratios. Table I shows the percent of Band I polymers found at various reaction states of aluminum chlorhydrate preparation when prepared by the conventional method.

TABLE I

| Aluminum/Chloride Atomic Ratio | % Band I Aluminum Polymers |
| --- | --- |
| 1.32:1 | 15.9 |
| 1.82:1 | 17.0 |
| 1.93:1 | 37.2 |

In addition to the formation of Band I, it is also known that basic aluminum halides produced via conventional methods of synthesis contain lower amounts of Band III than those amounts found using the process of this invention.

Figure 2B:
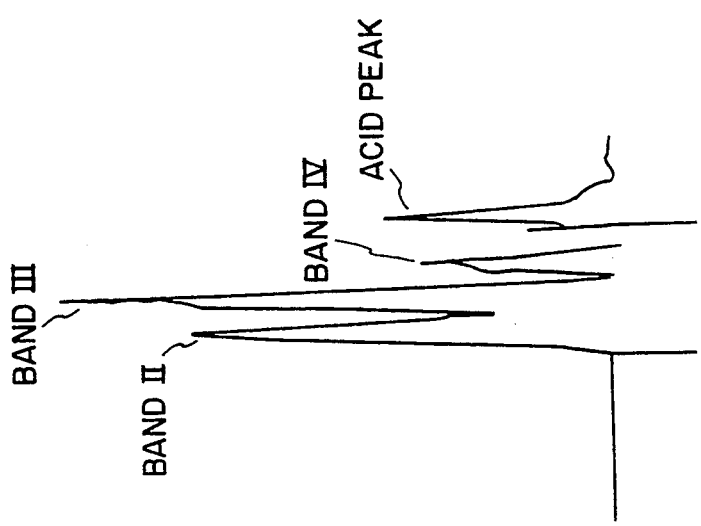
Figure 2C:
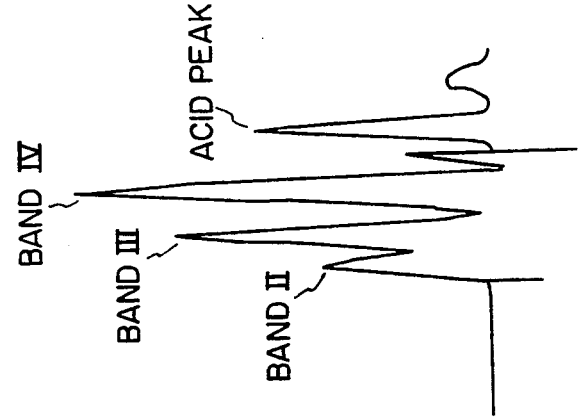
Figure 2D:
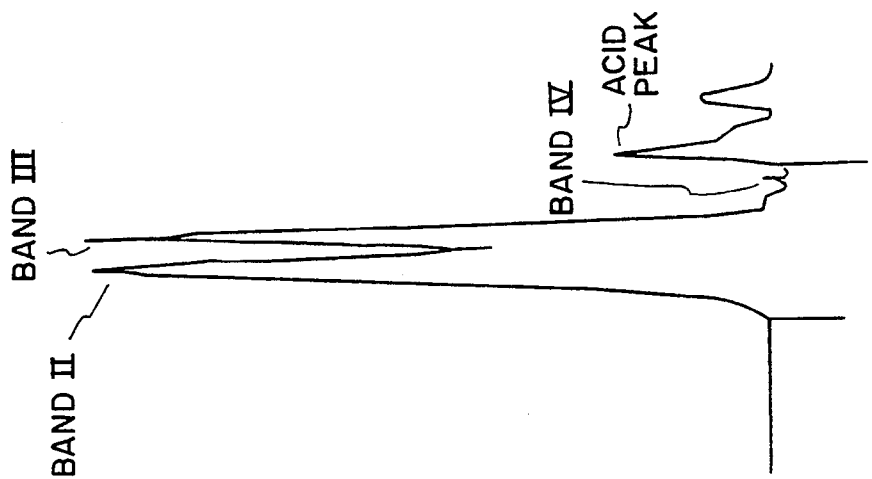
Figure 2E:
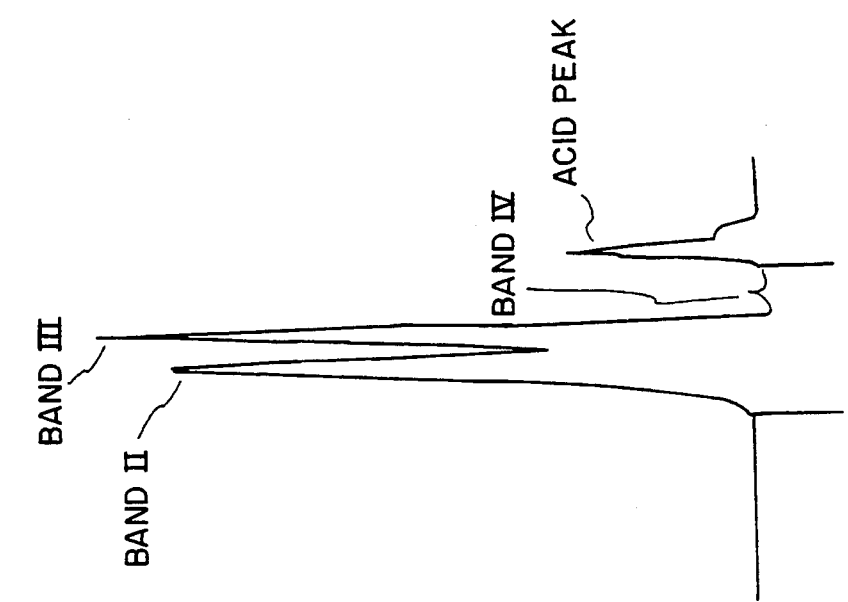
Figure 2F:
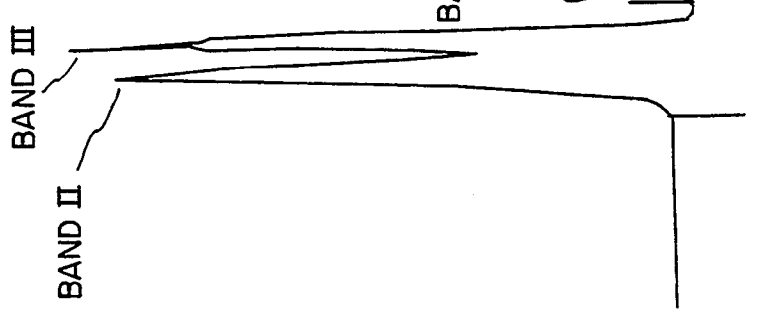

The advantages of the instant invention will be more readily appreciated by reference to the following example and the drawings. The examples are intended to be illustrative of the invention and in no way limit the scope of this invention. In the drawings FIGS. 1 and 2 illustrate chromatograms of the product showing the four (4) typical aluminum polymer bands. Example 1 describes a prior art process and is outside the scope of the invention.

EXAMPLE 1

Aluminum metal was reacted with hydrochloric acid and water, where the amount of water was stoichiometrically controlled so that the final reaction product contained a (water+hydroxyl)/aluminum molar ratio of about 9.7:1 and the active concentration was about 50%, as described below.

In a 250 ml glass reaction flask, equipped with a reflux condenser and thermometer, 30 g. of granulated aluminum was reacted with 125.8 grams of delonlzed water and 52 grams of 20 Baume hydrochloric acid. The batch was heated to 98° C. until nearly all the aluminum was in solution and the aluminum to chloride atomic ratio was determined by analysis to be 2.00:1. The resulting 50% solution was filtered and its polymer composition was determined by the size exclusion chromatogram test previously described. The chromatogram in FIG. 1 shows four typical aluminum containing polymer bands with relative retention times calculated with respect to the retention time of hydrochloric acid. Table II shows the retention times, relative retention times and the percent of the total aluminum polymers found in each band.

TABLE II

| Band | RI (Min) | RRT | AL Polymer |
| --- | --- | --- | --- |
| I | 3.72 | 0.65 | 39.23 |
| II | 4.08 | 0.72 | 54.98 |
| III | 4.38 | 0.77 | 2.95 |
| IV | 4.89 | 0.86 | 2.85 |

The last unintegrated band in FIG. 1 is that of hydrochloric acid which exists as free acid to some degree in all basic aluminum chlorides. In accordance with the test procedure described in the invention this peak was eluted at 5.7 minutes and it is this retention time that is used as the basis in calculating relative retention times of all other bands. The range of relative retention times for purposes of the invention has been defined as shown in Table III.

TABLE III

| Band No. | Relative Retention Time Range |
| --- | --- |
| Band I | 0.62–0.70 |
| Band II | 0.71–0.75 |
| Band III | 0.76–0.82 |
| Band IV | 0.83–0.97 |

The 50% solution obtained in this example is a standard product in the industry and can be marketed as such or further processed to a basic aluminum chloride powder through common techniques such as spray drying, vacuum drying, etc.

Example 2 illustrates the process of this invention.

EXAMPLE 2

946 grams of aluminum chloride hexahydrate 50% solution was charged to a 12 liter reaction flask. 4,830 grams of water and 718 grams of aluminum metal was charged to the flask and the contents were heated to 50° C. A mixture of 4,830 grams of water and 946 grams of aluminum chloride hexahydrate 50% solution was slowly added over 90 minutes. The reaction is exothermic, but additional heat was required to raise the temperature to 95° C., where it was maintained at that level throughout the reaction which was carried out over a seven day period. Although the reaction was carried out in the absence of reflux, a water cooled condenser was utilized to minimize water loss. Daily samples were taken to monitor the reaction process. The basicity of the reaction mixture increased as more aluminum metal was consumed. The polymer distribution of the product was determined for each sample using the method described above. After seven days the hot basic aluminum chloride solution was decanted off the excess unreacted aluminum. The hot solution was spray dried on a conical bottom laboratory unit utilizing a 400° F. inlet temperature and a 210° F. outlet temperature. 2.41 kg. of an off white crystalline powder was recovered which was analyzed for percent aluminum, chloride, aluminum/chloride ratio and polymer distribution. No additional water was added to the reaction mixture during the reaction. However, it will be appreciated by those skilled in the art that in a commercial process the condenser would not be used, but instead additional water would be added to maintain a relatively constant reactant/product concentration in the reactor.

Figure 3C:
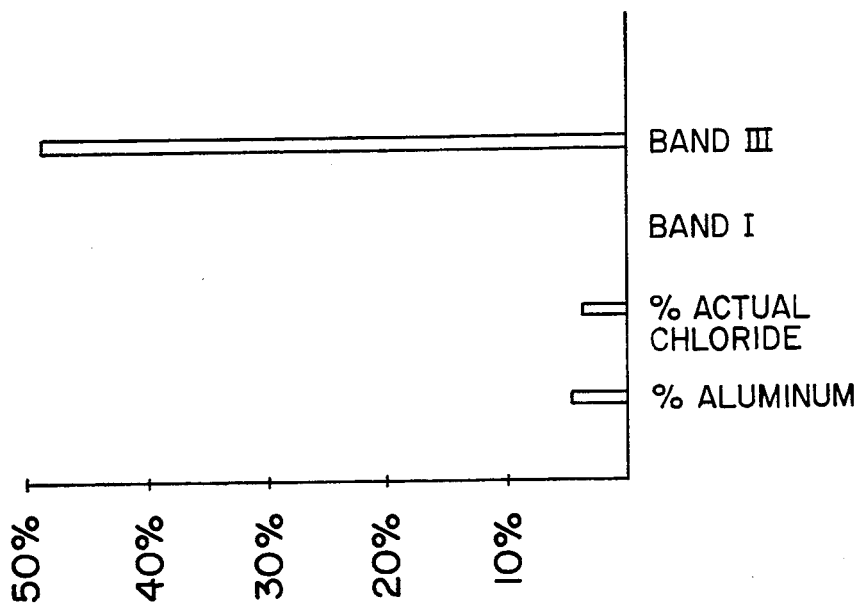
FIG. 3A-F is a bar chart of the analysis of the Product of Example 2.
Figure 3B:
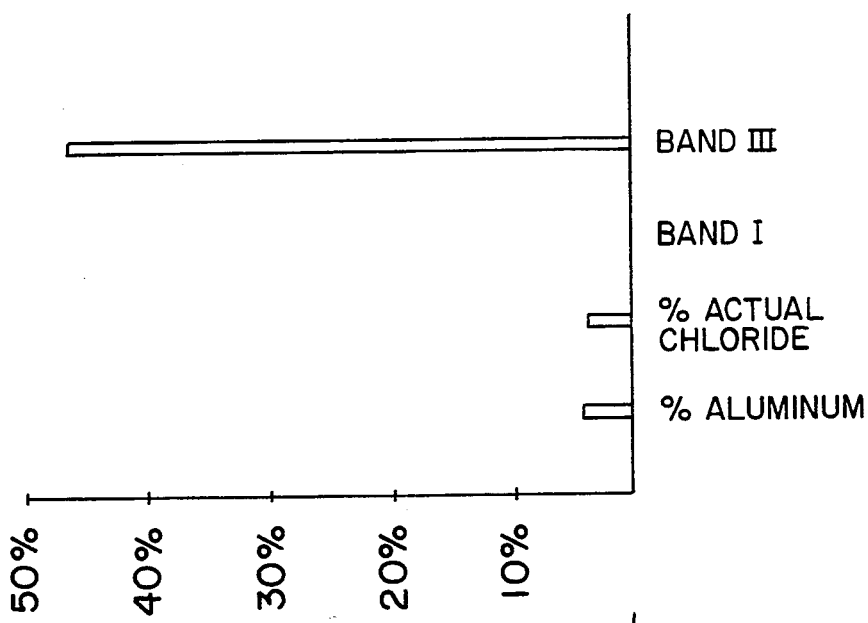
Figure 3A:
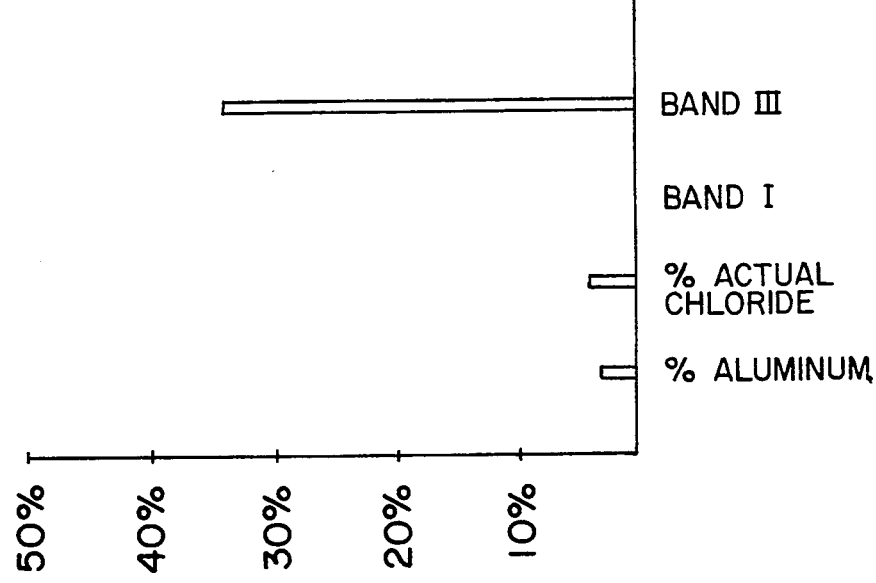
Figure 3F:
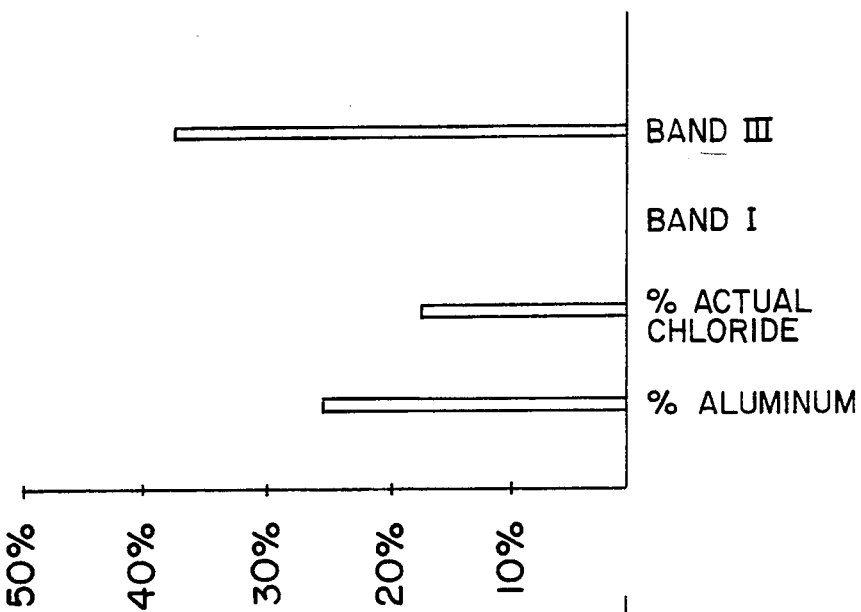
Figure 3E:
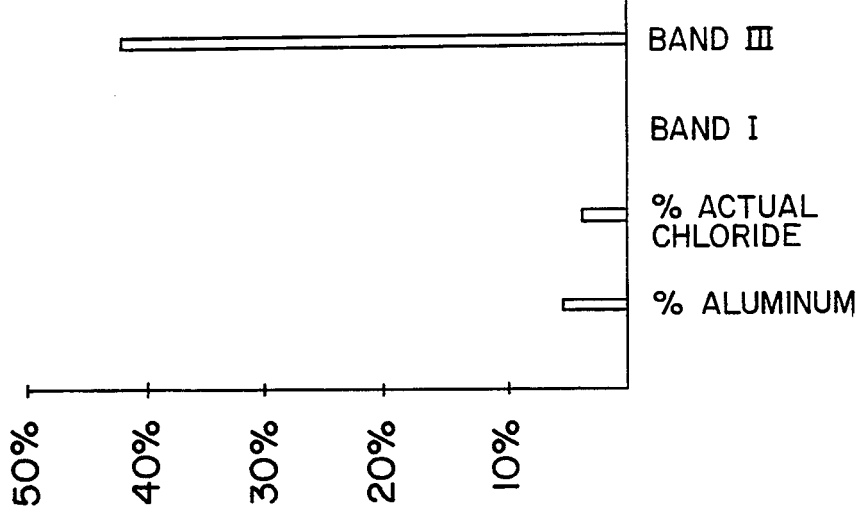
Figure 3D:
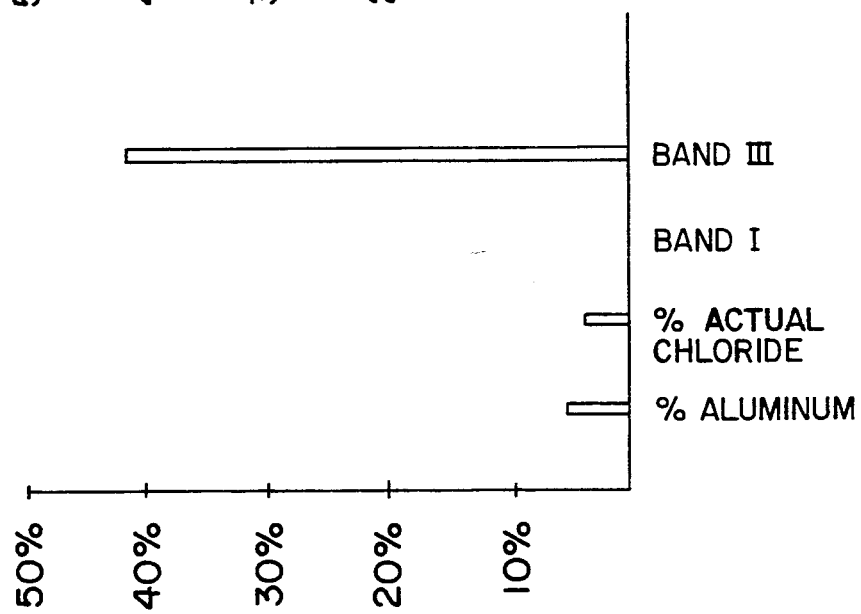

The powder comprised 25.80% aluminum, 17.10% chloride and had an Al/Cl atomic ratio of 1.98:1. The polymer distribution analysis showed that 100% of the polymers existed in the II, III & IV bands with 0% in Band I and 37.89% in Band III. Chromatograms 2A–2F show band distribution change during the reaction stages. As the reaction progresses there is a depletion of Band IV and a concomitant formation of bands II and III from lower molecular weight polymers. No band I is ever developed. In FIG. 3 the concentration of Aluminum, Chloride and Band III are shown as bar graphs.

The Al/halide ratio can be adjusted by adding additional aluminum chloride hexahydrate to the product solution before drying to recover product.

The invention provides a reaction process for the preparation of polymeric basic aluminum halides where Band I is not formed, and at least 25% of the composition is found in Band III. A narrow distribution of polymers of low molecular weight is obtained where 100% of the aluminum containing polymers fall within chromatographic Bands II, III & IV as defined by the relative retention time ranges using the test method described within the invention. In the process of this invention no Band I component ever exists, unlike prior art processes which begin with a product containing Band I and convert the starting material to a high band III component product.

What is claimed is:

1. A process for preparing a basic aluminum halide having the empirical formula:

$$Al_2(OH)_{6-y}X_y \cdot nH_2O$$

where n has a numerical value of about 0.8 to about 4, X is chlorine, bromine or iodine and y has a numerical value of about 0.7 to about 3, which comprises:
   (a) reacting aluminum metal with an aluminum halide hexahydrate having the formula $AlX_3 \cdot 6H_2O$ wherein X is chlorine, bromine or iodine by heating in water at a temperature of about 50° C. to about 100° C., the concentration of the product in the solution being about 8 to about 25% by weight of the solution; and
   (b) recovering the basic aluminum compound from the hot solution by spray drying;
whereby the polymer distribution of the product formed as characterized by size exclusion chromatography is:
   (c) 100% of the polymers are found in Bands II, III and IV, with no part of the product found in Band I; and
   (d) Band III contains at least 25% of the polymer.

2. The process according to claim 1 wherein the reaction is carried out in the absence of reflux at a temperature of about 80° C. to about 100° C.

3. The process according to claim 1 wherein the reaction is carried out at a temperature of about 95° C. to about 100° C.

4. The process according to claim 1 wherein the reaction is carried out at a temperature of about 96° C. to about 98° C.

5. The process according to claim 1 wherein the aluminum halide hexahydrate is aluminum chloride hexahydrate or aluminum bromide hexahydrate.

6. The process according to claim 1 wherein the aluminum halide hexahydrate is aluminum chloride hexahydrate.

7. The process according to claim 1 wherein the aluminum is in the form of pellets or powder.

8. The process according to claim 1 wherein the aluminum contains copper in an amount of about 0.005 to about 0.03 wt. %.

9. The process according to claim 1 wherein the aluminum contains iron in an amount of about 0.02 to about 0.1 wt. %.

10. The process according to claim 1 wherein the concentration of product in solution is about 15 to about 25% by weight.

11. The process according to claim 1 wherein the concentration of product in the solution is about 17 to 22% by weight.

12. The process according to claim 1 wherein the aluminum is present in excess of the stotchiometric amount calculated on the aluminum halide utilized.

13. The process according to claim 1 wherein the reaction is terminated and the Al/halide ratio is adjusted by adding additional aluminum chloride hexahydrate to the product solution before drying to recover product.

14. The process according to claim 1 wherein the concentration of product in solution is less than 15 wt. % and the reaction temperature is about 70° to about 85° C.

15. The process according to claim 1 wherein the process is carried out in the absence of reflux.

16. A process for preparing a basic aluminum halide having the empirical formula:

$$Al_2(OH)_{6-y}X_y \cdot nH_2O$$

where n has a numerical value of about 0.8 to about 4, X is chlorine, bromine or iodine and y has a numerical value of about 0.7 to about 3, which comprises:
(a) reacting aluminum metal with an aluminum halide hexahydrate having the formula $AlX_3 \cdot 6H_2O$ wherein X is chlorine, bromine or iodine at a temperature of about 50° C. to about 100° C., the concentration of the product in the solution being about 8 to about 25% by weight of the solution, said aluminum containing a reaction catalyst comprising metal wherein the metal is copper utilized at about 0.005 to about 0.2 wt. %, or iron utilized at about 0.02 to about 0.25 wt % based on the weight of aluminum; and
(b) recovering the basic aluminum compound from the hot solution by spray drying;
whereby the polymer distribution of the product formed as characterized by size exclusion chromatography is:
(c) 100% of the polymers are found in Bands II, III and IV, with no part of the product found in Band I; and
(d) Band III contains at least 25% of the polymer.

17. The process according to claim 16 wherein the reaction is terminated and the Al/halide ratio is adjusted by adding additional aluminum chiefide hexahydrate to the product solution before drying to recover product.

18. The process according to claim 16 wherein the copper is utilized at about 0.005 to about 0.03 wt %.

19. The process according to claim 16 wherein the iron is utilized at about 0.02 to about 0.1 wt %.

20. The process according to claim 16 wherein the reaction catalyst is copper.

21. The process according to claim 16 wherein the reaction catalyst is iron.

22. The process according to claim 16 wherein the reaction is carried out in the absence of reflux at a temperature of about 80° C. to about 100° C.

23. The process according to claim 16 wherein the reaction is carried out at a temperature of about 95° C. to about 100° C.

24. The process according to claim 16 wherein the reaction is carried out at a temperature of about 96° C. to about 98° C.

25. The process according to claim 16 wherein the aluminum halide hexahydrate is aluminum chloride hexahydrate or aluminum bromide hexahydrate.

26. The process according to claim 16 wherein the aluminum halide hexahydrate is aluminum chloride hexahydrate.

27. The process according to claim 16 wherein the aluminum is in the form of pellets or powder.

28. The process according to claim 16 wherein the concentration of product in solution is about 15 to about 25% by weight.

29. The process according to claim 16 wherein the concentration of product in the solution is about 17 to 22% by weight.

30. The process according to claim 16 wherein the aluminum is present in excess of the stoichiometric amount calculated on the aluminum halide utilized.

31. The process according to claim 16 wherein the aluminum halide concentration in the solution is at least three percent by weight.

32. The process according to claim 16 wherein the spray drying is carried out using a spray drier outlet temperature of about 150° F. to about 275° F.

33. The process according to claim 16 wherein the spray drying is carried out using a spray drier outlet temperature of about 200° F. to about 240° F.

34. The process according to claim 16 wherein the spray drying is carried out using a spray drier outlet temperature of about 210° F. to about 230° F.

35. The process according to claim 16 wherein the concentration of product in the solution is about 8 to about 15 wt. %, the reaction temperature is maintained at about 75° C. to about 85° C. and the reaction time is less than 24 hrs.

36. The process according to claim 16 wherein the reaction is carried out in the absence of reflux.

* * * * *